US 6,659,986 B1

(12) United States Patent
Nilstein

(10) Patent No.: US 6,659,986 B1
(45) Date of Patent: Dec. 9, 2003

(54) CONTAINER DEVICE FOR COLLECTING URINE

(76) Inventor: Carola Nilstein, Kampementsgatan 28, Stockholm (SE), SE-115 28

( * ) Notice: Subject to any disclaimer, the term of this patent is extended or adjusted under 35 U.S.C. 154(b) by 0 days.

(21) Appl. No.: 09/529,755
(22) PCT Filed: Oct. 19, 1998
(86) PCT No.: PCT/SE98/01874
   § 371 (c)(1),
   (2), (4) Date: Jul. 31, 2000
(87) PCT Pub. No.: WO99/20219
   PCT Pub. Date: Apr. 29, 1999

(30) Foreign Application Priority Data

Oct. 17, 1997 (SE) .................................................. 9703796

(51) Int. Cl.$^7$ ................................................. A61M 1/00
(52) U.S. Cl. ................... 604/317; 604/329; 604/349; 4/144.1; 4/144.2; 4/144.3
(58) Field of Search ................... 604/329, 328, 604/349, 346, 347, 355, 317; 4/144.1–144.4; 383/44

(56) References Cited

U.S. PATENT DOCUMENTS

| 4,305,161 A | * | 12/1981 | Diaz | 4/144.2 |
| 4,790,834 A | * | 12/1988 | Austin | 604/349 |
| 4,820,291 A | * | 4/1989 | Terauchi et al. | 604/349 |
| 4,868,024 A | * | 9/1989 | Cross et al. | 428/35.2 |
| 4,996,727 A | * | 3/1991 | Wyatt | 4/484 |
| 5,007,116 A |   | 4/1991 | Yamamoto |  |
| 5,009,236 A | * | 4/1991 | Brothers | 128/761 |
| 5,013,309 A | * | 5/1991 | Baigas, Jr. et al. | 604/368 |
| 5,353,805 A | * | 10/1994 | Mojena | 128/761 |
| 5,354,132 A | * | 10/1994 | Young et al. | 383/49 |
| 5,662,630 A | * | 9/1997 | Raynie | 604/349 |
| 5,961,501 A | * | 10/1999 | Cassidy et al. | 604/327 |

FOREIGN PATENT DOCUMENTS

| EP | 0494599 A2 | 7/1992 |
| WO | 9203994 A1 | 3/1992 |
| WO | 9500183 A1 | 1/1995 |

* cited by examiner

Primary Examiner—Weilun Lo
Assistant Examiner—Jacqueline F Stephens
(74) Attorney, Agent, or Firm—Leo Stanger

(57) ABSTRACT

The present invention relates to a container device (1) for collecting urine. The container device comprises a holding member (5), a flexible container (1), connected to the holding member (5), which is arranged to receive the urine and a superabsorbent powder (4) enclosed is said flexible container, (1) and arranged to make the urine congeal. Said superabsorbent powder (4) is enclosed in the flexible container (1), in a package (3) which is manufactured in a urine soluble material.

27 Claims, 3 Drawing Sheets

CONTAINER DEVICE FOR COLLECTING URINE

TECHNICAL FIELD OF THE INVENTION AND PRIOR ART

The present invention relates to a container device for collecting urine, which comprises a flexible container arranged to receive the urine and a superabsorbent powder enclosed in said flexible container and arranged to make the urine congeal.

From U.S. Pat. No. 5,007,116 such a container device is previously known. A liquid absorbing means is in this case enclosed in a bag of a paper or fabric material in a flexible container having a mouthpiece. When the urine flows down in the flexible container and reaches the bag it penetrates the bag material with the result that the liquid absorbing material swells and the bag is brooken. The disadvantage with such bags is that they not are absolutely tight and a fine granulated superabsorbent powder may in a dry state leak through such a bag material and be diffused in the flexible container. Another disadvantage with the container device according to U.S. Pat. No. 5,007,116 is that the mouthpiece and the flexible container are manufactured in one piece. Thereby, the container device is relatively large to carry around, expensive to manufacture and constitutes an unnecessarily great strain on the environment because the whole container device is thrown away after use.

From EP 0 494 599 a superabsorbent composition is known which is arranged to make body fluids congeal, for example blood received from surgical operations. The superabsorbent composition comprises a superabsorbent powder having a grain size of 5 mm, which is enclosed in a bag of a water-soluble film, which may comprise polyvinyl alcohol. In this document, nothing is mentioned about the use of this super absorbing composition in order to congeal urine and especially not by means of a container device of the kind initially mentioned.

From the Swedish patent application 9703796-4 a container device for collecting urine is known, which comprises a funnel and a bag releasably connected to the funnel and arranged to receive the urine. After the bag is filled with urine, it is thrown away and a new bag may be connected to the funnel. The disadvantage with this container device is that a bag filled with urine is very difficult to handle and the risk is great that urine splashes out of the bag. Furthermore, said funnel takes up a relatively large space and is thereby cumbersome to carry around.

On the market there are also a plurality of different types of flexible bags for collecting urine but these have also the disadvantage that the urine easily is splashed out during the handling of the bags.

SUMMARY OF THE INVENTION

The object of the present invention is to provide a container device for collecting urine, which above all is easy to handle, also for handicapped persons, without the urine splashing out of the flexible container. Other objects are that it should be easy carry around, inexpensive to manufacture and harmless to the environment.

The object is achieved by the initially mentioned container device, which is characterised in that said superabsorbent powder is enclosed, in the flexible container, in a package manufactured in a urine soluble material. Thereby is obtained that the powder in a dry state is safely kept in the package without the risk that it diffused in the flexible container. Furthermore, by a suitable choice of material and thickness of the material, such a package may be, so quickly soluble in the urine that the superabsorbent powder with only a small time delay may be dispersed in the urine and made it congeal to a gelatinous mass. Thereby, is in an effective way prevented that the urine splashes out of the bag during its handling. The total time to make 500 ml of urine congeal may not exceed 70 sec, which is the time for a normal emptying of a normal volume of urine. Consequently, during a normal emptying, the urine has congealed when the emptying time is over.

According to a preferred embodiment of the present invention, said package is at least partly manufactured of polyvinyl alcohol. Polyvinyl alcohol is a material which is essentially completely tight, at least concerning said superabsorbent powder, at the same time as it is highly soluble in urine. In order to obtain the congealing time mentioned above, the polyvinyl alcohol may have a thickness of material of between 15–60 $\mu$m. Consequently, the thickness of the material ought not to exceed 60 $\mu$m because in that case it takes too long time for the urine to dissolve the material and preferably not be below 15 $\mu$m because in that case the material risks to be destroyed during a somewhat careless handling. In order to obtain an extremely quick congealing time of the urine the superabsorbent powder may be in granulate form and have an average grain size of 200 $\mu$m or less. By such a grain size, the amount of the superabsorbent powder may be reduced and thereby also the size of the package.

According to another preferred embodiment of the present invention, it comprises a holding member, which is releasably connectable to the flexible container. Thereby, the use of the container device by women is facilitated. By a holding member, it is possible to hold an opening of the flexible container steadily in a position suitable for the emptying of urine. After use, the flexible container may be released from the holding member in order to be thrown away while the holding member may be saved. Thereafter, the holding member may be re-used with a new flexible package. For a user, this means that a holding member only needs to be procured at a first shopping occasion and thereafter one only needs to buy flexible containers containing a package of the superabsorbent powder. Thereby, the product is cheaper per time of use and the environment is not strained by unnecessary single use material. Furthermore, a holding member which may be used a plurality of times may be more sumptuous, and may for example be formed more form-fit and in a more solid material, than if it where of single use type. In order to connect the flexible container releasably to the holding member, the portion of the flexible container, which comprises an opening, may be passed through a passage in the holding member. Thereafter, the side portions of the flexible container, which are located around the opening of the flexible container, are folded down around an upper edge at the entrance of the passage of the holding member. In many cases, such a connection between the flexible container and the holding member may be completely sufficient to guarantee that the flexible container does not come loose from the holding member during the use of the container device. Alternatively, the holding member may comprise means arranged to enable a releasable connection between the flexible container and the holding member. Such means may be a hole provided in the holding member, which is arranged to receive a portion of the flexible container when it is connected to the holding member. Thereafter, a user may move a finger down into said hole in order to secure that the flexible container is held in a connected state to the holding member during the emptying of urine. An alternative means may comprise an elastic member or the like, which resiliently abuts the flexible container in a state connected to the holding member and thereby secures that it does not come loose. Preferably, the flexible container is manufactured of a thin film of a plastic material. Such a plastic bag has the advantages that it may be manufactured at a low cost and that it is completely liquid tight.

According to another preferred embodiment of present invention, the holding member comprises a handle. Thereby, the container device may be held steadily in an exactly correct position so that the urine during the emptying is guided down into the passage of the holding member and the risk that it lands outside the flexible container is negligible. Advantageously, the holding member comprises a portion, at an upper entrance of the passage of the holding member, which has a shape anatomically adapted for women in order to completely guarantee that the urine is guided down through the passage of the holding member. Said shape ought to be such that the holding member without problem may be used in both a sitting and a standing position. For men solely a bag without any holding member may be used or a holding member of a simpler shape may be used, which-consists of an essentially ring-shaped construction.

BRIEF DESCRIPTION OF THE DRAWINGS

In the following preferred embodiments of the invention are described as example with reference to the attached drawings, in which.

DETAILED DESCRIPTION OF PREFERRED EMBODIMENTS OF THE PRESENT INVENTION

Figure 1:
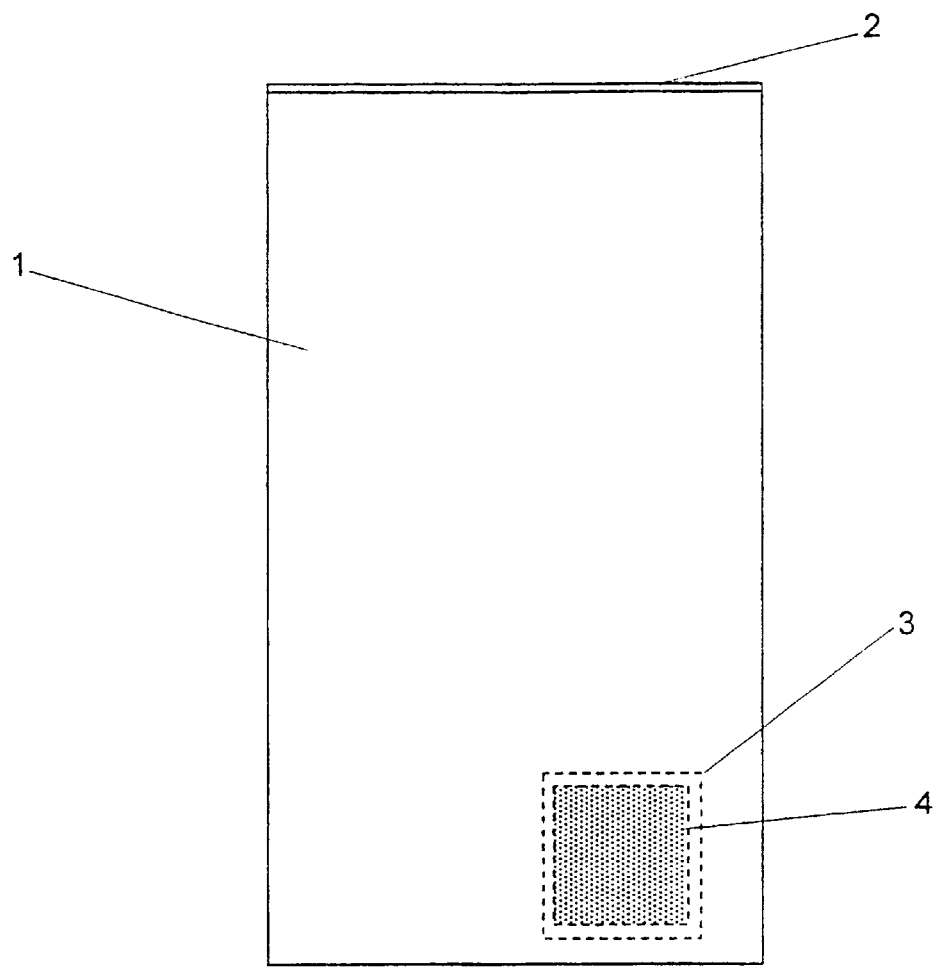
FIG. 1 shows a flexible container, according to the present invention, shaped as a bag.

FIG. 1 shows a flexible container according to the present invention in the shape of a bag 1 manufactured of a thin plastic material, which advantageously is non-transparent and has an upper opening 2. The bag 1 encloses a package 3 which itself encloses a granulated superabsorbent powder 4. The package 3. is wholly or partly manufactured of polyvinyl alcohol which is easily soluble in urine and sufficiently tight in order to effectively prevent that the dry granulated superabsorbent powder 4 leaks out through the walls of the package 3 into the bag 1. If a dry superabsorbent powder 4 leaks out into the bag 1, it is collected on. the inner walls of the bag 1, wherein it, when urine flows down in the container 1, whirl around by the air streams formed during the emptying, in such a way that powder particles risk to get caught to the user.

Figure 2:
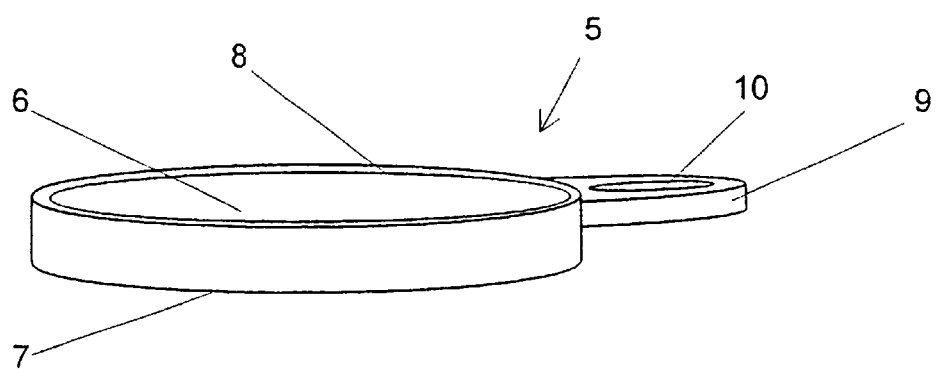
FIG. 2 shows a holding member according to the present invention.
Figure 3:
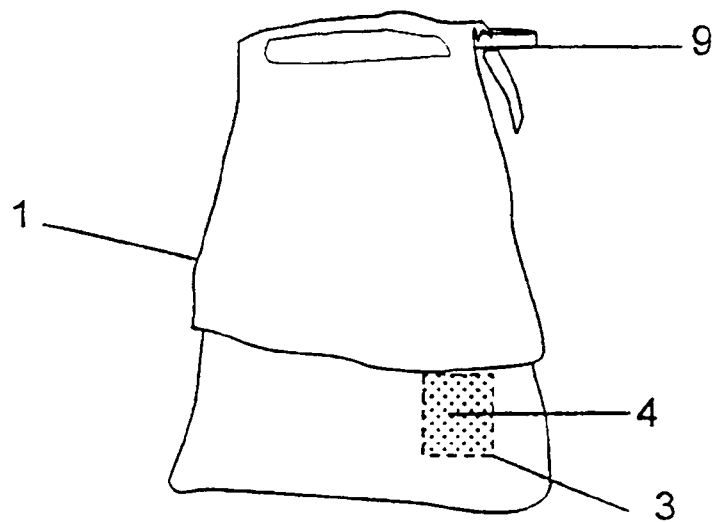
FIG. 3 shows a holding member connected to a bag according to the present invention.
Figure 4:
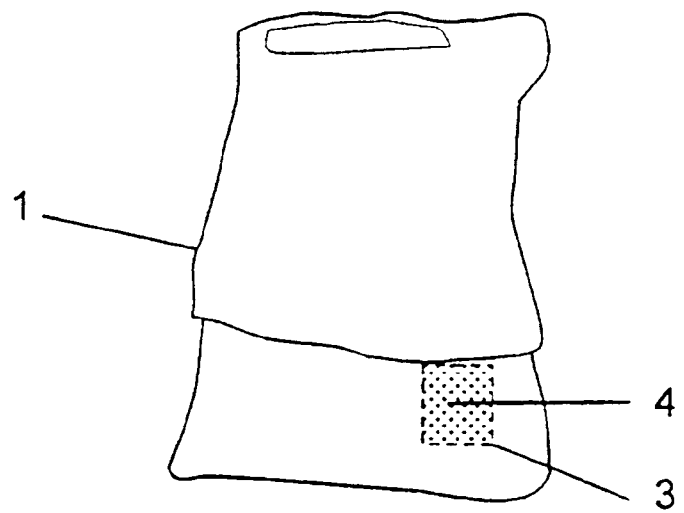
FIG. 4 shows a holding member connected to a bag according to an alternative embodiment.

For men it is completely sufficient to carry around the above described bag 1, shown in FIG. 1. However, for women it is difficult to hold the opening 2 of the flexible bag 1 steadily in an emptying position in such a way that no urine lands outside the bag 1. In FIG. 2 a holding member 5 is shown, which is releasably connected to the bag 1 with the purpose to facilitate for women to hold the opening 2 of the bag 1 steadily in a suitable position for the emptying of urine. The holding member 5 is essentially ring-shaped and comprises a passage 6 having a lower opening 7 and an upper opening 8. Such a holding member. 5 has an essentially, ring-shaped construction with a relatively large passage 6, which is oval. Such a simple holding member 5 is easy to carry around, for example in a handbag. The holding member 5 may also comprise a handle 9, which preferably is small, by which it may be held securely and steadily in an intended position in such a way that the urine securely is guided down through the passage 6 of the holding member 5 and down into the bag 1. FIG. 3 shows a holding member 5 connected to a bag 1. The holding member 5 may be connected to the bag 1 in that an upper portion of the bag 1, which comprises the opening 2, is passed from below through the passage 6 of the holding member 5, whereafter the side portions of the opening 2 are folded down externally over the holding member 5. In the connected state of the bag 1 to the holding member 5, a portion of the bag 1 may be passed through a hole 10 in the handle. Thereafter, the user may keep a finger in the hole in order to secure that the bag 1 does not come loose from the holding member during the emptying of urine into the bag 1. The holding member 5 shown in FIG. 2 may be used by women in both a standing and a sitting position during the emptying of urine. FIG. 4 shows a holding member 5 connected to a bag 1 according to an alternative embodiment. After the bag 1 has been guided through the passage 6 of the ring-shaped holding member 5, the upper portion of the bag 1 is folded over both the holding member 5 and the handle 9. Thereafter, the bag 1 is kept in place in that the user holds the handle 9.

The package 3 is a completely closed package and may be formed as a bag. Advantageously, the package 3 consists of polyvinyl alcohol or essentially a polyvinyl alcohol film having a thickness of between 10–100 $\mu$m, preferably 15–60 $\mu$m, and having a package volume of between 15–300 cm$^3$, preferably 15–200 cm$^3$, comprising 10–100 g, preferably 15–75 g superabsorbent powder, which has a theoretical absorption capacity during a free swelling in synthetic urine of between 20–120 times its own weight, preferably 30–100 times its own weight, with an average grain size of 200 $\mu$m, preferably 150 $\mu$m or less.

According to a first embodiment of the package 3, it may constitute a completely closed rectangular package 3 in the dimension 50×60 mm, consisting of a 25 $\mu$m thick film of polyvinyl alcohol type L.330 from Aquafilm ltd filled with 28 g superabsorbent powder of the type Salsorb 10 Fines from Allied Collids having an average grain size of 150 $\mu$m.

According to a second embodiment, the package 3 comprises a bag having the dimensions 50×100 mm, consisting of a 40 $\mu$m thick film of polyvinyl alcohol type Aquafilm ltd filled with 40 g superabsorbent powder of the type Gelling agent 31 Fines from Allied Colloids, having an average size size of 200 $\mu$m.

Figure 5:
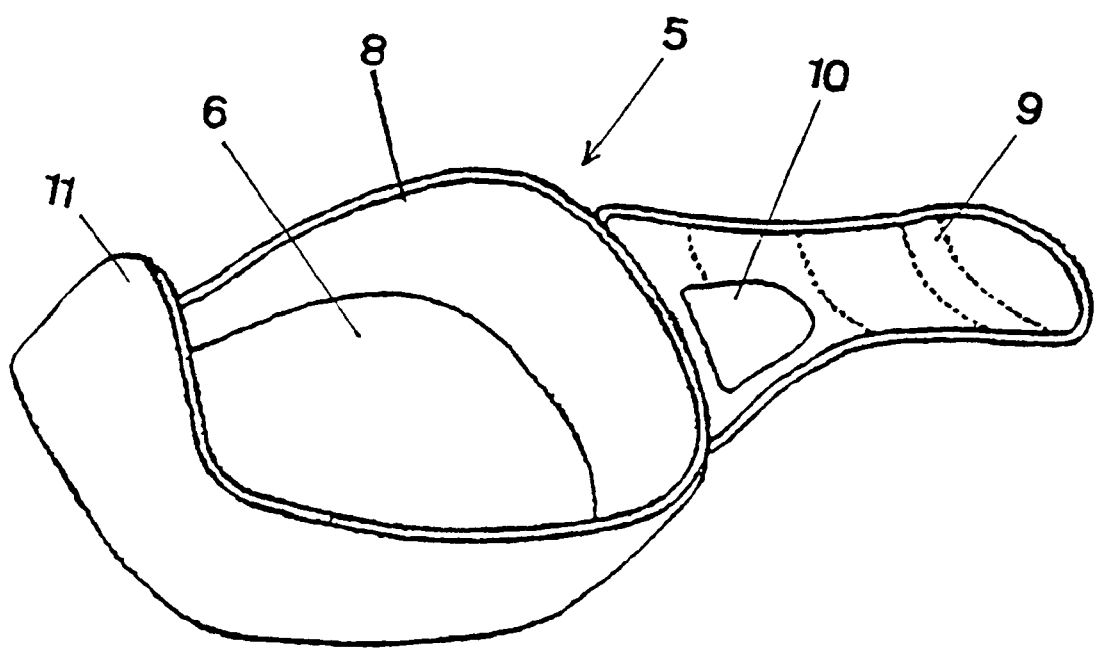
FIG. 5 shows an alternative embodiment of a holding member.

An alternative embodiment of a holding member 5 is shown. in FIG. 5. This holding member 5 is especially directed towards Women, which have to relieve themselves sitting, for example women carried by wheelchairs. Therefore, the holding member 5 has a shape anatomically adapted for women. The passage 6 of the holding member 5 thereby comprises an elongated upper opening 8 and the holding member 5 an upwardly projecting rear portion 11, which is arranged to guarantee that the flow of urine is guided downwardly in the passage 6. The handle 9 according to this embodiment also comprises a hole 10.

By the use of a container device according to the present invention, a suitable holding member 5 and a package, which advantageously comprises a plurality of bags 1 of a non-transparent plastic material, each of which comprises a package 3 having a granulated superabsorbent powder 4, are bought at a first occasion. Such a package may be made very small with the bags 1 folded up. Therefore, the package is easy to carry around. Thereby, the user may in critical situations and when need arises connect a bag 1 to the holding member 5, which may be performed in that an upper portion of the bag 1, comprising the opening 2, is passed from below through the passage 6 of the holding member 5, whereafter the side portions of the opening 2 are folded down externally over the holding member 5. In this connection, the user may with a finger press down a portion of the bag, 1 into the hole 10 in the handle, whereby the bag 1 is kept safely connected to the holding member 5. Thereafter, the holding member 5 is moved to a suitable position for the emptying of urine and is steadily kept in this position by means of the handle 9, in such a way that all outflowing urine may be guided down into the flexible container 1 by means of the holding member 5. The package 3 of polyvinyl alcohol, which is placed in the bag 1, is thereby dissolved and deformed by the urine, in such a manner that the enclosed granulated superabsorbent powder 4 flows out and is mixed with the urine. Thereby, the superabsorbent powder 4 swells in such a way that the urine congeals to a gelatinous mass. The total time for the urine to congeal thus consists in the deformation time for the package 3 and the swelling time for the superabsorbent powder in the urine to form a gelatinous mass. The package 3 thereby has such a thickness and the superabsorbent powder 4 has such a grain size that an amount of 500 ml of urine is congealed within 70 sec. i.e. a normal time for the emptying of a normal volume of urine. Thereby is obtained that essentially all urine has congealed when the emptying is over. Thereby, the user may immediately after the emptying release the bag 1 from the holding member 5 without risking that urine splashes out of the bag 1. Thereafter, the upper portion of the bag 1 may be tied together whereafter the bag 1 with the gelatinous urine may be disposed in the nearest waste container or the like.

However, the user keeps the holding member 5 in order to use it together with a new bag 1 at the next occasion. Consequently, in the future the user needs only buy new bags 1 of the above mentioned type, wherby the cost for the user per occasion may be kept at a low level.

The invention is not in any way restricted to the embodiments of the invention shown in the figures but may be modified and varied freely within the scope of the claims. The material comprising the package 3 may be other materials than polyvinyl alcohol, for example other polymer materials, cellulose- and/or starch based materials etc. Above, women and men are mentioned as users of the container device according to the invention but it is also usable for children of different ages.

What is claimed is:

1. A container device arranged to be used by a person for collecting urine, which device comprises a flexible container arranged to receive the urine and a superabsorbent powder enclosed in said flexible container and arranged to make the urine congeal, characterised in that:

said superabsorbent powder is enclosed, in the flexible container, in a package manufactured in a urine-soluble material and in that the container device comprises a releasably connectable holding member, which is arranged to hold an entry opening of the flexible container steadily in a position suitable for the emptying of urine; the holding member is releasably connected to the container, the container includes an upper portion having the entry opening, the upper portion passes through the passage of the holding member, and the upper portion is folded down externally over the holding member.

2. A container device according to claim 1 characterised in that said package at least partly is manufactured of polyvinyl alcohol.

3. A container device according to claim 2, characterised in that superabsorbent powder is in granulate form.

4. A container device according to claim 2, characterised in that the superabsorbent powder has an average grain size of 200 $\mu$m or less.

5. A container device according to claim 2, characterised in that said holding member comprises means arranged to enable said releasable connection between the flexible container and the holding member.

6. A container device according to claim 2, characterised in that the flexible container is manufactured of a thin film of a plastic material.

7. A container device according to claim 2, characterised in that the holding member comprises a handle.

8. A container device according claim 2, characterised in that the holding member comprises at the upper opening a portion having a shape anatomically adapted for women.

9. A container device according to claim 1, characterised in that said material has a thickness between 10–100 $\mu$m.

10. A container device according to claim 9, characterised in that superabsorbent powder is in granulate form.

11. A container device according to claim 9, characterised in that the superabsorbent powder has an average grain size of 200 $\mu$m or less.

12. A container device according to claim 9, characterised in that said holding member comprises means arranged to enable said releasable connection between the flexible container and the holding member.

13. A container device according to claim 1, characterised in that superabsorbent powder is in granulate form.

14. A container device according to claim 13, characterised in that the superabsorbent powder has an average grain size of 200 $\mu$m or less.

15. A container device according to claim 13, characterised in that said holding member comprises means arranged to enable said releasable connection between the flexible container and the holding member.

16. A container device according to claim 1, characterised in that said holding member comprises means arranged to enable said releasable connection between the flexible container and the holding member.

17. A container device according to claim 1, characterised in that the flexible container is manufactured of a thin film of a plastic material.

18. A container device according to claim 1, characterised in that the holding member comprises a handle.

19. A container device according claim 1, characterised in that the holding member comprises at the upper opening a portion having a shape anatomically adapted for women.

20. A container device according to claim 1, characterised in that said material has a thickness between 15–60 $\mu$m.

21. A container device as in claim 1, wherein said releasably connected holding member is removable from the container to permit separate disposal of said container.

22. A container device as in claim 1, wherein said releasably connected holding member is applied to the container for use during urination and removable from the container to permit separate disposal of said container.

23. A container device as in claim 22, wherein said releasably connected holding member is rigid.

24. A container as in claim 1, wherein the holding member is ring-shaped and comprises a passage having a lower opening and an upper opening.

25. A container as in claim 1, wherein the holding member has a ring-shaped construction with a relatively large oval passage.

26. A container as in claim 25, wherein the holding member includes a handle for grasping the holding member securely and steadily in an intended position in such a way that the urine securely is guided down through the passage of the holding member and down into the container.

27. A container as in claim 26, where the handle forms a hole for holding an edge of the container so a user may keep a finger in the hole in order to secure that the container does not come loose from the holding member during the emptying of urine into the container.

* * * * *